(12) United States Patent
Bennett, III et al.

(10) Patent No.: US 7,577,553 B2
(45) Date of Patent: Aug. 18, 2009

(54) METHOD AND APPARATUS FOR MOLECULAR MECHANICS ANALYSIS OF MOLECULAR SYSTEMS

(75) Inventors: Forrest H. Bennett, III, Palo Alto, CA (US); William Mydlowec, Palo Alto, CA (US)

(73) Assignee: Numerate, Inc., San Bruno, CA (US)

( * ) Notice: Subject to any disclaimer, the term of this patent is extended or adjusted under 35 U.S.C. 154(b) by 733 days.

(21) Appl. No.: 10/452,481

(22) Filed: May 30, 2003

(65) Prior Publication Data

US 2004/0010525 A1 Jan. 15, 2004

Related U.S. Application Data

(60) Provisional application No. 60/395,155, filed on Jul. 10, 2002.

(51) Int. Cl.
*G06F 17/10* (2006.01)
(52) U.S. Cl. ........................................................ 703/2
(58) Field of Classification Search ...................... 703/2
See application file for complete search history.

(56) References Cited

U.S. PATENT DOCUMENTS

| | | | |
|---|---|---|---|
| 5,424,963 A | 6/1995 | Turner et al. | |
| 5,425,036 A | 6/1995 | Liu et al. | |
| 5,448,496 A | 9/1995 | Butts et al. | |
| 5,452,231 A | 9/1995 | Butts et al. | |
| 5,612,891 A | 3/1997 | Butts et al. | |
| 5,657,241 A | 8/1997 | Butts et al. | |
| 5,661,662 A | 8/1997 | Butts et al. | |
| 5,734,581 A | 3/1998 | Butts et al. | |
| 5,796,623 A | 8/1998 | Butts et al. | |
| 5,812,414 A | 9/1998 | Butts et al. | |
| 5,841,967 A | 11/1998 | Sample et al. | |
| 5,870,316 A | 2/1999 | Gilbert et al. | |
| 6,002,861 A | 12/1999 | Butts et al. | |
| 6,026,422 A | 2/2000 | Yamada et al. | |
| 6,058,492 A | 5/2000 | Sample et al. | |
| 6,112,288 A | 8/2000 | Ullner | |
| 6,205,533 B1 | 3/2001 | Margolus | |

OTHER PUBLICATIONS

Amisaki et al.; Development of hardware accelerated board for molecular dynamics simulations: a computation board that calculates nonbonded interactions in cooperation with fast multipole method; abstract; J Comput. Chem. Apr. 2003.*

Simmler, H. et al., Acceleration of Protein Energy Calculation by FPGAs, METMBS '00 Internatinal Conference: 177-183 (2000).

Toyoda, Shinjiro et al., Development of MD Engine: High-Speed Accelerator with Parallel Processor Design for Molecular Dynamics Simulations, Journal of Computational Chemistry, vol. 20, No. 2:185-199 (1999).

(Continued)

*Primary Examiner*—Hugh Jones
(74) *Attorney, Agent, or Firm*—Moser IP Law Group

(57) ABSTRACT

A method and apparatus for analyzing molecular systems with reconfigurable special-purpose hardware is provided. An entire molecular mechanics calculation is implemented on a programmable logic device (PLD) integrated circuit (IC) ("single chip"). This single IC accelerator is achieved by run-time reprogramming of the PLD to handle different terms in the molecular mechanics calculation.

8 Claims, 1 Drawing Sheet

OTHER PUBLICATIONS

Workshop schedule and Abstract Summary: ERCIM WG Matrix Computations and Statistics, pp. 1-2 and 8 (2002).

Shackleford, B. et al., An FPGA-Based Genetic Algorithm Machine, Eighth ACM>International Symposium on Field-Programmable Gate Arrays, Poster Abstracts (2000).

Halgren, Thomas A., MMFF VI. MMFF94s Option for Energy Minimization Studies, Journal of Computational Chemistry, vol. 20, No. 7: 720-729 (1999).

Halgren, Thomas A., Merck Molecular Force Field. I. Basis, Form, Scope, Parameterization, and Performance of MMFF94, Journal of Computational Chemistry, vol. 17, Nos. 5 & 6: 490- 519 (1996).

Chen, Doug et al., The QCDSP project-a status report, Nuclear Physics B (Proc. Suppl.) 60A: 241-245(1998).

Lemoine, Eric and Merceron, David, Run Time Reconfiguration of FPGA for Scanning Genomic DataBases, IEEE: 90-98 (1995).

Jorgensen, William L. et al, Development and Testing of the OPLS All-Atom Force Field on Conformational Energetics and Properties of Organic Liquids, J. Am. Chem. Soc. 118: 11225-11236 (1996).

Dimmler, D.G. et al., Fastrun —A High Performance Computing Device for Molecular Mechanics Using a Pipeline Architecture, IEEE Transactions on Nuclear Science, vol. 33, No. 1: 870-874 (1986).

Fine, Richard et al., Fastrun: A Special Purpose, Hardwired Computer for Molecular Simulation, Proteins: Structure, Function, and Genetics 11: 242-253 (1991).

Fukushige, Toshiyuki et al., A Highly Parallelized Special-Purpose Computer for Many-Body Simulations With an Arbitrary Central Force: MD-GRAPE, The Astrophysical Journal 468: 51-61 (1996).

Hamada, Tsuyoshi et al., PROGRAPE-1: A Programmable, Multi-Purpose Computer for Many-Body Simulations, Publ. Astron. Soc. Japan 52: 943-954 (2000).

Bakker, A.F. et al., A Special Purpose Computer for Molecular Dynamics Calculations, Journal of Computational Physics 90: 313-335 (1990).

Ito, Tomoyoshi et al., A Special-Purpose Computer for $N$-Body Simulations: GRAPE-2A, Publ. Astron. Soc. Japan 45: 339-347 (1993).

Bakker, A.F. and Bruin, C., Design and Implementation of the Delft Molecular-Dynamics Processor, Special Purpose Computers, pp. 183-232 (1988).

T. Fukushige, et al., "Wine-1: Special Purpose Computer for N-Body Simulations with a Periodic Boundary Condition", Publs. Astron. Soc. Japan, 45, pp. 361-375, 1993.

Tetsu Narumi; "Special-Purpose Computer for Molecular Dynamics Simulations", Doctoral thesis, Department of General Systems Studies, College of Arts and Sciences, University of Tokyo, Dec. 1997.

Martin Gerber, et al., "HAM: Hardware Moved Molecules Annual Report 1997", Swiss Federal Institute of Technology, TIK Report No. 38, 1997, pp. 1-74, Zürich, Switzerland.

* cited by examiner

METHOD AND APPARATUS FOR MOLECULAR MECHANICS ANALYSIS OF MOLECULAR SYSTEMS

This application claims priority to Provisional Application Ser. No. 60/395,155, filed Jul. 10, 2002.

FIELD OF THE INVENTION

The invention relates generally to molecular analysis, and more particularly to molecular mechanics analysis of molecular systems.

BACKGROUND OF THE INVENTION

Molecular mechanics algorithms are used to simulate physical properties of molecular systems such as free energy changes, salvation energy, intra-atomic forces, binding energies of ligand/target complexes or other host/guest complexes. Examples of molecular mechanics algorithms include MMFF94, OPLS, AMBER, MM4, and CHARMM. The energy of a molecular system is computed as the sum of component energy terms. There are local energy terms and there are non-bonded energy terms. The typical local energy terms used are the bond energy between two atoms, the angular bond energy between three atoms, and the dihedral angle energy between four atoms. Typical non-bonded energy terms are the electrostatic energy between pairs of non-bonded atoms, and the van der Waals energy between pairs of non-bonded atoms. Other local energy terms may also be included such as improper torsion angle energy, out-of-plane bending energy, Urey-Bradly energy, angle stretch-bend energy, and the like. The force on each atom is the derivative of the energy on the atom. The second derivative of the energies of all the atoms, the Hessian matrix, is sometimes calculated for use in minimization procedures.

In conventional molecular mechanics algorithms, the non-bonded interactions between pairs of atoms are computed for every pair of atoms in the molecular system except intramolecular interactions between pairs of atoms separated by fewer than some threshold number of bonds, and intramolecular interactions between pairs of atoms separated by exactly a certain number of bonds are weighted by some factor. These intramolecular interactions are referred to as "nearby non-bonded" interactions. In other words, nearby, as used herein means at least two atoms separated by fewer than some threshold number of bonds, including, but not limited to, pairs of atoms separated by exactly a certain number of bonds.

The non-bonded interaction terms, van der Waals energy and the electrostatic interaction are the most time consuming part of a molecular system energy calculation, because the non-bonded terms are computed between each atom and every other atom in the molecular system. That is, in such calculations the non-bonded terms are $O(N^2)$ (order $n^2$) in the number of atoms. Therefore, the non-bonded terms are more important terms to accelerate, as compared to the local terms which are $O(N)$ (order n) in the number of atoms.

However, accelerating the local interaction terms is still important. Typically in molecular mechanics calculations, the local interaction calculations take approximately 1% of the time of the total calculation, and the non-bonded interaction calculations take approximately 99% of the time of the total energy calculation. Therefore, it is generally assumed that only the non-bonded calculations need to be accelerated. However, this assumption is specious. For example, suppose the total calculation takes 1 second and that an accelerator gives a factor of 100 times speed increase to the non-bonded part of the calculation. This would mean that the non-bonded part of the calculation changes from 0.99 seconds to 0.0099 seconds, and the local part of the calculation stays at 0.01 seconds. So the accelerated total calculation time is 0.0099+0.01=0.0199 seconds, or approximately 0.02 seconds. But 0.02 seconds is 1/50th of the original time of 1 second. Therefore, the overall calculation time was only reduced by a factor of 50 even though the non-bonded part of the calculation was sped up by a factor of 100.

Moreover, this discrepancy between acceleration of the non-bonded part of the calculation as compared with acceleration of the overall calculation increases as the acceleration factor increases. That is, if the local part of the calculation is not accelerated, then there are diminishing returns on accelerating the non-bonded part of the calculation. Consider another example to illustrate the problem using the above assumption of relative percentages of time for non-bonded and local energy and force, which may or may not include second derivative calculations. Suppose the total calculation takes 1 second and that an accelerator gives a factor of 1000 speedup to the non-bonded part of the calculation. This would mean that the non-bonded part of the calculation changes from 0.99 seconds to 0.00099 seconds, and the local part of the calculation stays at 0.01 seconds. So the accelerated total calculation time is 0.00099+0.01=0.01099 seconds, or approximately 0.01 seconds. But 0.01 seconds is 1/100th of the original time of 1 second. Therefore the overall calculation time was only reduced by a factor of 100 even though the non-bonded part of the calculation was sped up by a factor of 1000.

These examples show the importance of speeding up the local part of the calculation even though it typically takes only 1% of the time in a standard implementation. The examples also make apparent that it becomes more important to speed up the local part of the calculation the greater the acceleration of the non-bonded part of the calculation.

To accelerate the calculation of energies and forces for a molecular system others have tried:

force calculation and time integration implemented with a microprogram in PROM coupled to TTL-compatible components with fixed point calculations (see, e.g., A. F. Bakker and C. Bruin, Design and implementation of the Delft molecular-dynamics processor, in Special Purpose Computers; edited by B. J. Alder. Academic Press, San Diego, Calif., pp. 183-232 (1988));

floating point calculations implemented with an LSI, using a downloaded microprogram for force calculation (see, e.g., A. F. Bakker, G. H. Gilmer, M. H. Grabow, and K. Thompson, A Special Purpose Computer for Molecular Dynamics Calculations, J. Comp. Phys., 90: 313-335 (1990));

a special purpose hardwired computer for calculating non-bonded forces, coulomb force, coulomb potential, Van der Waals force and Van der Waals potential (see, e.g., R. Fine, G. Dimmler, and C. Levinthal, FASTRUN: A Special Purpose, Hardwired Computer for Molecular Simulation, Proteins, 11:242-253 (1991); or D. G. Dimmler, R. Fine, and C. Levinthal; FASTRUN:A High Performance Computing Device for Molecular Mechanics Using a Pipeline Architecture; BNL 37221; Nuc. Sci. Symp., 22-25 October (1985), San Francisco, Calif.; IEEE Trans. Nuc. Sci. NS-33, No. 1, Febrary (1986) 870-874);

a special purpose computer for calculating non-bonding force, using a single pipeline (see, e.g., T. Ito, J. Makino, T. Fukushige, T. Ebisuzaki, S. K. Okumura, and D. Sugimoto, A Special-Purpose Computer for N-Body Simulations: GRAPE-2A. Pubis, Astron. Soc. Japan, 45: 339-348 (1993));

a special purpose computer for calculating the wave-space part of the Ewald method with fixed point calculations for DFT and IDFT (see, e.g., T. Fukushige, J. Makino, T. Ito, S. Okumrua, T Ebisuzaki, and D. Sugimoto, WINE-1: Special-Purpose Computer for N-body Simulations with a Periodic Boundary Condition, Publs., Astron. Soc. Japan, 45: 361-375 (1993));

LSI for calculating non-bonded force, Van der Waals force or potential from neighbor lists generated in the boards with coefficients stored in off-LSI memory (see, e.g., S. Toyoda, H. Miyagawa, K. Kitamura, T. Amisaki, E. Hashimoto, H. Ikeda, A. Kusumi, and N. Miyakawa, Development of MD Engine: High-Speed Accelerator with Parallel Processor Design for Molecular Dynamics Simulations, Journal of Computational Chemistry, 20,2: 185-199 (1999));

LSI for calculating non-bonding force, real-space coulomb force, wavenumber-space coulomb force, DFT, IDFT with coefficients stored in off-ASIC memory (see, e.g., T. Fukushige, M. Taiji, J. Makino, T. Ebisuzaki, and D. Sugimoto, A Highly-Parallelized Special-Purpose Computer for Many-body Simulations with an Arbitrary Central Force: MD-GRAPE, Astrophysical Journal, 468: 51-61 (1996)); and LSI calculations for non-bonded forces only, with less than 100 floating point operations per chip with Van der Waals coefficients stored on chip and 32 atom types per chip (see, e.g., T. Narumi, Special-purpose computer for molecular dynamics simulations, Doctoral thesis, Department of General Systems Studies, College of Arts and Sciences, University of Tokyo (1998)).

More recently, investigators have gotten away from special purpose computers and large scale integrations turning to programmable logic devices (PLDs), such as field programmable gate arrays (FPGAs). Some investigators have used an FPGA for a non-bonded calculation (see, e.g., T. Hamada, T. Fukushige, A. Kawai, and J. Makino, PROGRAPE-1: A Programmable, Multi-Purpose Computer for Many-Body Simulations, Publ. Astron. Soc. Japan 52:943-954 (2000)), and for two-dimensional lattice and for contact potential (non-molecular mechanics) (see, e.g., B. Shackleford, D Carter, G Snider, E. Okushi, M. Yasuda, H. Kozizumi, K. Seo, T. Iwanoto, and H Yasuura, An FPGA-Based Genetic Algorithm Machine, Eighth ACM International Symposium on Field-Programmable Gate Arrays(2000); and H. Simmler, E. Bindewald, R. Manner, Acceleration of Protein Energy Calculation by FPGAs, Proc. of the Int. Conf. on Mathem. and Engineering Techniques in Medicine and Biological Sciences (METMBS'00), Las Vegas, 177-183 (2000)). In addition, run-time reconfiguration of a field programmable gate array has been described in E. Lemoine, and D. Merceron, Run Time Reconguration of FPGA for Scanning Genomic Data Bases, IEEE Symposium on FPGAs for Custom Computing Machines, pp. 90-98 (1995).

Substantial cost savings, as well as time-to-market enhancement, may be achieved by using PLDs. Heretofore, a PLD has not been used to implement both non-bonded and local calculations for a molecular mechanics function. However, as explained above, a substantial advantage may be obtained by accelerating both non-bonded and local calculations. Accordingly, it would be both desirable and useful to provide the molecular mechanics calculation implemented on a single PLD.

SUMMARY

An aspect of the present invention is to provide methods and apparatus for analyzing molecular systems that are faster than those currently known in the art. It is a further aspect of the present invention to provide methods and apparatus for analyzing molecular systems in which the step of testing for nearby non-bonded interactions between atoms is not required in the inner loop of the non-bonded term calculations. When the testing for nearby non-bonded interactions is removed from the inner loop, the bandwidth requirements of the calculation are reduced, thereby reducing the size of the non-bonded inner loop pipelines so that additional non-bonded inner loop pipelines can fit on the chip and increasing the speed of the calculation.

Other aspects of the present invention include methods and apparatus to compute non-bonded terms while ignoring nearby non-bonded interactions. A separate computation is then done to calculate the nearby non-bonded interactions. The nearby non-bonded energy is then subtracted from the total energy of the system, and for each atom the nearby non-bonded forces are subtracted from the force on that atom.

It is a further aspect of the present invention that all terms in a molecular mechanics calculation be implemented in a single chip, by reconfiguring the chip for different sets of interaction terms. The time taken to configure the chip is much less than the time it takes to calculate the energies and forces, therefore the overall processing time is still very fast in spite of the time taken for chip reconfiguration. The local part of the calculation requires roughly four times as many numerical operations as the non-bonded part of the calculation. Therefore, if hardware resources are naively applied to acceleration it would cost four times as much to speed up the local part of the calculation, even though the hardware is only used for 1% of the total calculations that need to be done. To avoid spending four times as much on hardware to accelerate 1% of the calculation, the method and apparatus of the present invention use reconfigurable hardware. By reconfiguring the hardware, less hardware is used but the overall calculation is still accelerated. The hardware dedicated primarily to calculating the non-bonded terms, but is still available to accelerate the local terms.

BRIEF DESCRIPTION OF THE DRAWINGS

So that the manner in which the above-recited features, advantages and objects of the present invention are attained and can be understood in detail, a more particular description of the invention, briefly summarized above, may be had by reference to the embodiments that are illustrated in the appended drawing and described in the present specification. It is to be noted, however, that the appended drawing illustrates only a typical embodiment of this invention and is therefore not to be considered limiting of its scope, for the present invention may admit to other equally effective embodiments.

DETAILED DESCRIPTION

Figure 1:
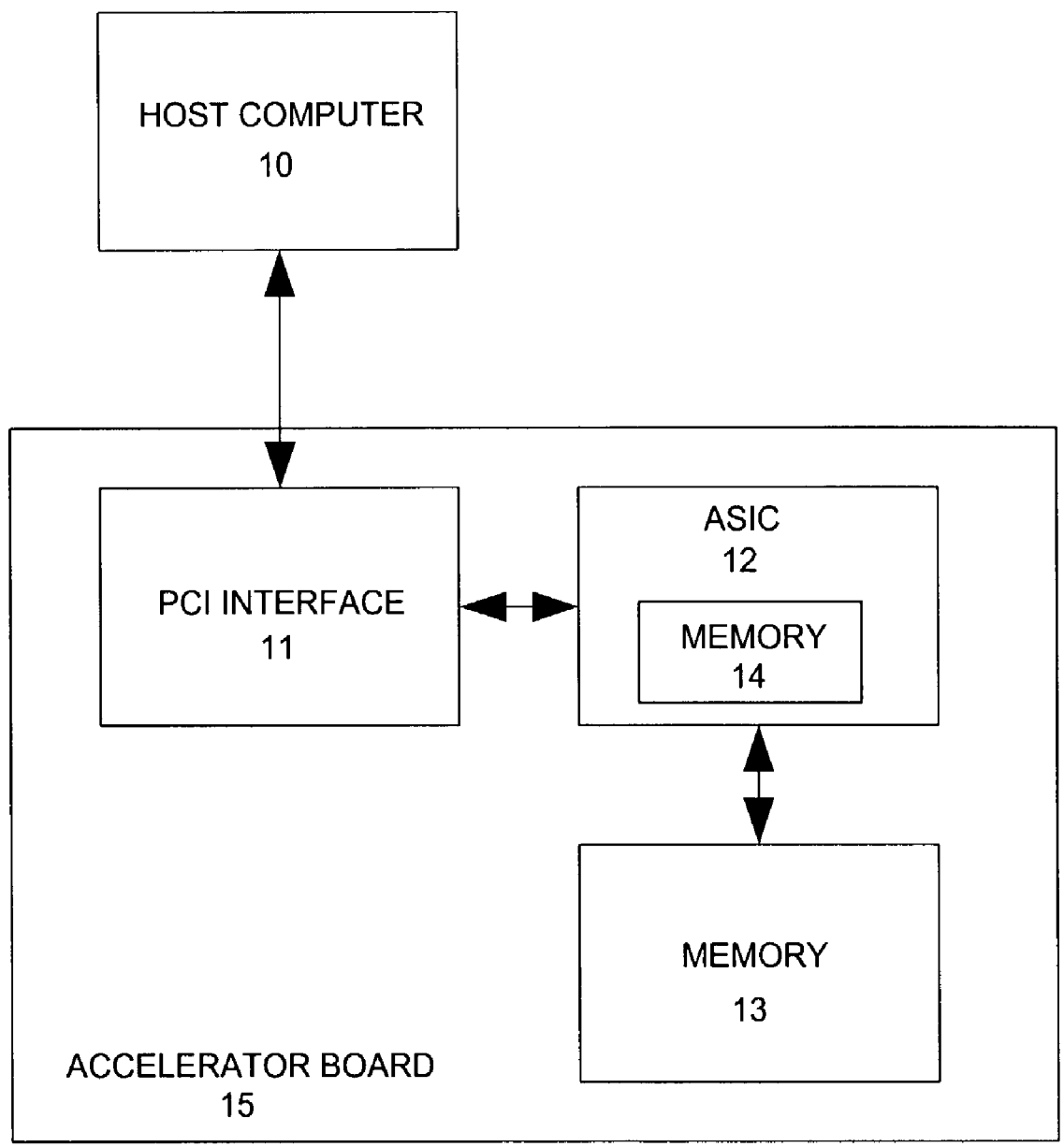
FIG. 1 is a block diagram of an exemplary embodiment of an accelerator coupled to a host computer in accordance with one or more aspects of the present invention.

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

Steps are described for computing an exemplary molecular mechanics algorithm. Such algorithms are known in the art, and can be found, for example, in T. Halgren, Merck Molecular Force Field, Basis, Form, Scope, Parameterization, and Performance of MMFF94, J. Comput. Chem., 17:490-519 (1996); T. Halgren, MMFF VI. MMFF94s Option for Energy Minimization Studies. J. Comp. Chem. 20:720-729 (1999); and W. Jorgensen, D. Maxwell, and J. Tirado-Rives, Development and Testing of the OPLS All-Atom Force Field on Conformational Energetics and Properties of Organic Liquids, J. Am. Chem. Soc., 118:11225-11236 (1996). However, though molecular interactions may comprise energy, force and second derivative terms, either singly or in combination, only energy and force are described herein for purposes of clarity. Still, it should be readily apparent to those with skill in the art in view of the description of the force terms that second derivative terms may likewise be used:

- Input numerical data for molecular system. Numerical input data includes, for each atom in the molecular system, the x, y, and z coordinates of the atom, the type of the atom, and the partial charge of the atom.
- Generate topology information. Topology information may be generated, for example, by performing the following:
  - Compute for each atom in the molecular system a list of all the other atoms that are less than a given threshold bond distance from that atom;
  - Compute for each atom in the molecular system a list of all the other atoms that are exactly at a given threshold bond distance of that atom;
  - Compute a list of all pairs of bonded atoms;
  - Compute a list of all atom triples that form bond angles; and
  - Compute a list of all atom quadruples that form torsion angles.
- Compute a list of parameters including bond parameters for each bond pair, angle parameters for each angle, torsion parameters for each torsion angle, and van der Waals parameters for each atom.
- Referring to FIG. 1, host 10 via PCI interface 11 transmits the numerical data, the lists of atoms that are less than the given threshold distance, atoms that are at the given threshold distance, all pairs of bonded atoms, all atom triples that form bond angles, and all atom quadruples that form torsion angles for the molecular system to accelerator board 15. All this data may be stored in memory 13 on accelerator board 15.
- Host 10 initializes the total energy for the molecular system to zero.
- Host 10 initializes all forces for all atoms to zero in memory 14.
- Host 10 reconfigures FPGA 12 for the non-bonded calculation.
- Host 10 transmits van der Waals parameters and a table of atomic masses to memory 14.
- Host 10 starts the non-bonded calculation on FPGA 12.
- FPGA 12 adds the forces for each atom to memory 14.
- When the calculation is done, host 10 reads the non-bonded energy result from memory 14 of FPGA 12.
- Host 10 adds the non-bonded energy to the total energy for the molecular system.
- Host 10 reconfigures FPGA 12 for the nearby non-bonded energy calculation.
- Host 10 transmits van der Waals parameters and a table of atomic masses to memory 14.
- Host 10 starts the nearby non-bonded calculation on FPGA 12.
- FPGA 12 adds the forces for each atom to memory 14.
- When the calculation is done, host 10 reads the nearby non-bonded energy result from memory 14 of FPGA 12.
- Host 10 subtracts the nearby non-bonded energy from the total energy for the molecular system.
- Host 10 reconfigures FPGA 12 for the bond energy calculation.
- Host 10 transmits bond parameters to memory 14.
- Host 10 starts the bond energy calculation on FPGA 12.
- FPGA 12 adds the forces for each atom to memory 14.
- When the calculation is done, host 10 reads the bond energy result from memory 14 of FPGA 12.
- Host 10 adds bond energy to the total energy for the molecular system.
- Host 10 reconfigures FPGA 12 for the angle energy calculation.
- Host 10 transmits angle parameters to memory 14.
- Host 10 starts the angle energy calculation on FPGA 12.
- FPGA 12 adds the forces for each atom to memory 14.
- When the calculation is done, host 10 reads the angle energy result from memory 14 of FPGA 12.
- Host 10 adds the angle energy to the total energy for the molecular system.
- Host 10 reconfigures FPGA 12 for the torsion energy calculation.
- Host 10 transmits torsion parameter to memory 14.
- Host 10 starts the torsion energy calculation on FPGA 12.
- FPGA 12 adds the forces for each atom to memory 14.
- When the calculation is done, host 10 reads the torsion energy result from memory 14 of FPGA 12.
- Host 10 adds the torsion energy to the total energy for the molecular system.
- Host 10 reads the forces on all the atoms from memory 14.

Similarly, other interaction terms can be included such as improper torsion angle interaction, out-of-plane bending angle interaction, Urey-Bradly interaction, angle stretch-bend interaction, and the like.

Thus, the non-bonded calculation computes the non-bonded terms without skipping or weighting nearby pairs of atoms. This means that no tests are needed to detect the nearby atoms during the calculation.

For example, consider the OPLS molecular mechanics energy algorithm. Consider computing the electrostatic interaction for atom A. In OPLS, atoms that are one bond away and two bonds away from atom A are not included in the electrostatic calculation, and atoms that are three bonds away are weighted by a factor of 0.5. Every atom can be connected to as many as four other atoms. Therefore every atom has potentially four atoms one bond away, 12 atoms two bonds away, and 36 atoms three bonds away. Thus, for OPLS, there can be as many as 4+12=16 atoms that would not be included in the non-bonded interaction, and 36 atoms that would have their non-bonded energy weighted by a factor of 0.5. Thus, it would require as many as 4+12+36=52 tests to detect the nearby atoms that should be either not included or weighted. Such tests would slow the hardware down and take up space that could otherwise be dedicated to numerical calculations. Also, it would require up to 52 additional memory I/O operations to get the data for the nearby atoms needed to perform the tests. With the present invention, however, these additional memory I/O's are avoided so that each pipeline can produce the non-bonded energy and forces for one pair of atoms on each hardware clock cycle.

If there are n atoms in a molecular system, then for non-bonded terms there are n*(n−1)/2 iterations to perform, as the non-bonded calculation must be performed for each of the n atoms multiplied by each of the other atoms (n−1), and divided by 2 (to avoid adding the contribution for each pair of atoms twice). Instead of spending the time and space to perform the tests for nearby atoms on each of the atoms in the molecular system for each of the n*(n−1)/2 iterations, these tests are omitted such that interaction contributions of nearby atoms are not excluded and not weighted. Subsequently, an additional step is then taken to correct the energy and forces for the nearby atoms that should have been excluded and weighted in the calculation.

The non-bonded energy contribution of the nearby atoms is calculated separately and subtracted out of the total energy for the molecular system, and for each atom the non-bonded nearby force is subtracted out of the force for that atom. This is done for each atom A, 1) by iterating through the list of atoms that are less than the given threshold bond distance from A, and computing the non-bonded interaction for each atom on the list; and 2) by iterating through the list of atoms that are equal to the given threshold bond distance from A and computing the weighted non-bonded interaction for each atom on the list. The total of all these nearby non-bonded energies is computed on the hardware accelerator. The host reads this total and subtracts it from the total energy of the molecular system.

While the foregoing is directed to the preferred embodiment of the present invention, other and further embodiments of the invention may be devised without departing from the basic scope thereof, and the scope thereof is determined by the claims that follow. Claims listing steps do not imply any order of the steps, and all references cited herein are to aid in the understanding of the invention, and are incorporated in their entireties for all purposes.

The invention claimed is:

1. A system for performing molecular mechanics calculations for a molecular system, comprising:
    a programmable logic device configured to compute a non-bonded energy term for atoms within a molecular system without tests to detect and skip atom pairs that are within a predefined number of bonds from one another and without tests to detect and weight such atom pairs; and
    a computational system, coupled to the programmable logic device, for computing a nearby non-bonded energy correction term for atoms that are within the predefined number of bonds from one another, and correcting the non-bonded energy term with the nearby non-bonded energy correction term to generate a total non-bonded energy for the molecular system.

2. The system of claim 1, wherein the computational system further:
    computes a bond energy term for the molecular system; and
    adds the bond energy term to the total non-bonded energy.

3. The system of claim 2, wherein the computational system further:
    computes an angle energy term for the molecular system; and
    adds the angle energy term to the total non-bonded energy.

4. The system of claim 3, wherein the computational system further:
    computes a torsion energy term for the molecular system; and
    adds the torsion energy term to the total non-bonded energy.

5. The system of claim 1, wherein the programmable logic device further:
    reconfigures to a second configuration to be an element of the computational system that computes the nearby non-bonded energy correction term.

6. A system for performing molecular mechanics calculations for a molecular system defined by bonded atoms and non-bonded atoms, the system comprising:
    a field programmable gate array having a first gate array arrangement for performing a first computation that is reconfigured into a second gate array arrangement for performing a second computation, where either:
        a) the first computation computes a non-bonded energy term for atoms within a molecular system without tests to detect and skin atom pairs that are within a predefined number of bonds from one another and without tests to detect and weight such atom pairs and the second computation computes a nearby non-bonded energy correction term for atoms that are within the predefined number of bonds from one another, or
        b) the first computation computes a nearby non-bonded enemy correction term for atoms that are within the predefined number of bonds from one another and the second computation computes a non-bonded enemy term for atoms within the molecular system without tests to detect and skip atom pairs that are within a predefined number of bonds from one another and without tests to detect and weight such atom pairs; and
    a host computer, coupled to the field programmable gate array, for correcting the non-bonded energy term with the nearby non-bonded energy correction term to produce a total non-bonded energy of the molecular system.

7. The system of claim 6 wherein the field programmable gate array is reconfigured into different gate array arrangements to compute at least one of a bond energy term, an angle energy term or a torsion energy term, and the host adds the at least one of the bond energy term, the angle energy term or the torsion energy to the total energy term.

8. An system for performing molecular mechanics calculations for a molecular system, comprising:
    an ASIC configured to compute a non-bonded energy term for atoms within a molecular system without tests to detect and skip atom pairs that are within a predefined number of bonds from one another and without tests to detect and weight such atom pairs; and
    a computational system, coupled to the ASIC, for computing a nearby non-bonded energy correction term for atoms that are within the predefined number of bonds from one another, and correcting the non-bonded energy term with the nearby non-bonded energy correction term to generate a total non-bonded energy for the molecular system.

* * * * *

UNITED STATES PATENT AND TRADEMARK OFFICE
CERTIFICATE OF CORRECTION

PATENT NO. : 7,577,553 B2  Page 1 of 1
APPLICATION NO. : 10/452481
DATED : August 18, 2009
INVENTOR(S) : Bennett, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this

Seventh Day of September, 2010

David J. Kappos
*Director of the United States Patent and Trademark Office*